United States Patent [19]

Yoshida et al.

[11] Patent Number: 4,563,536

[45] Date of Patent: Jan. 7, 1986

[54] METHOD FOR SYNTHESIZING TRIOXANE

[75] Inventors: Koichi Yoshida; Toshiyuki Iwaisako; Junzo Masamoto; Katsuhiko Hamanaka, all of Fuji; Hajime Komaki, Kamakura, all of Japan

[73] Assignee: Asahi Kasei Kogyo Kabushiki Kaisha, Osaka, Japan

[21] Appl. No.: 425,040

[22] Filed: Sep. 27, 1982

Related U.S. Application Data

[62] Division of Ser. No. 233,414, Feb. 11, 1981, Pat. No. 4,381,397.

[30] Foreign Application Priority Data

Feb. 22, 1980 [JP] Japan ................................. 55-21988

[51] Int. Cl.$^4$ ........................................... C07D 323/06
[52] U.S. Cl. .................................................... 549/368
[58] Field of Search ......................................... 549/368

[56] References Cited

U.S. PATENT DOCUMENTS

| | | | |
|---|---|---|---|
| 3,149,127 | 9/1964 | Platz et al. | 549/368 |
| 3,347,869 | 10/1967 | Flodin et al. | 549/368 |
| 3,427,335 | 2/1969 | Herold | 549/368 |
| 3,483,214 | 12/1969 | Sperber et al. | 549/368 |
| 3,697,546 | 10/1972 | Asakawa et al. | 549/368 |
| 3,781,304 | 12/1973 | Fuchs et al. | 549/368 |

OTHER PUBLICATIONS

"Anorganische Chemie", F. A. Cotton/G. Wilkinson, Verlag Chemie, GmbH, W. Germany, 1968, pp. 876–884.

*Primary Examiner*—Ethel G. Love
*Attorney, Agent, or Firm*—Sprung, Horn, Kramer & Woods

[57] ABSTRACT

A method for synthesizing trioxane by heating and reacting an aqueous formaldehyde solution in the presence of a heteropolyacid. As the heteropolyacid, there is preferably used one that contains, as a coordinating element or coordinating elements, W, Mo, V or Nb alone or two or more of them.

13 Claims, No Drawings

METHOD FOR SYNTHESIZING TRIOXANE

This is a division of application Ser. No. 233,414, filed Feb. 11, 1981, now pending U.S. Pat. No. 4,381,397.

BACKGROUND OF THE INVENTION

1. Field of the Invention

This invention relates to a method for synthesizing trioxane, characterized by heating and reacting formaldehyde in the presence of a heteropolyacid.

2. Description of the Prior Art

This invention relates to a method for synthesizing trioxane from formaldehyde in the presence of a heteropolyacid.

Trioxane is a cyclic trimer of formaldehyde and is used mainly as a starting material for producing polyoxymethylene. In order to obtain polyoxymethylene having a satisfactory molecular weight, very pure trioxane is required and it is necessary that its contents in particular, of the so-called by-products such as water, formic acid and methanol which become chain transfer agents, methylal, methyl formate, and polyoxymethylenedimethoxide with a low molecular weight, and the like should be low.

Many researches have been done on a method for synthesizing trioxane satissfying these requirement, though a usual production method consists of obtaining trioxane by heating formaldehyde in the presence of an acid catalyst, for example, sulfuric acid, phosphoric acid, boric acid, benzenesulfonic acid, toluenesulfonic acid, an acidic ion-exchange resin, or the like, or in the presence of a solid acid catalyst such as aluminum sulfate, silica or the like. Among the above-mentioned catalysts, sulfuric acid is most generally used because the reaction rate is fast when it is used, and it is easily available. However the sulfuric acid method have involved several practical problems to be solved. For example, when the formaldehyde concentration exceeds 60% by weight, paraformaldehyde is formed, and when the sulfuric acid concentration is 8% by weight or higher, by-products such as formic acid, methyl formate and the like are formed so that the yield of trioxane is lowered. Further, when the sulfuric acid concentration is 10% by weight or higher, many by-products are formed, therefore it has been proposed to effect the reaction by adding a dispersing agent such as di-2-ethylhexyl phthalate, however the addition of the third component makes post-treatment and the like troublesome and hence is not thought to be a suitable method. As mentioned above, conventional methods have had many disadvantages for application on an industrial scale, for example, (1) many by-products are formed, (2) scales of paraformaldehyde tend to be formed in th reactor or on the wall of the distilling column, (3) the reactor and the wall of the distilling column are corroded.

SUMMARY OF THE INVENTION

The object of this invention is to find a reaction method free from various defects which conventional method have in the production of trioxane from formaldehyde, for example, (1) many by-products are formed, (2) scales of paraformaldehyde tend to be formed in the reactor or on the wall of the distilling column, (3) the reactor and the wall of the distilling column are corroded.

In order to accomplish the above-mentioned object, the present inventors have made various studies on the reaction method to find that when formaldehyde is heated and reacted in the presence of a heteropolyacid, the object can be accomplished, that is to say, (1) the trioxane content in the distillate obtained by distilling the reaction solution after the reaction is high, and its contents of by-products such as formic acid, methyl formate, methylal, methanol and the like are low, (2) when a high concentration of a heteropolyacid is present, the solubility of formaldehyde is increased so that it becomes possible to react an aqeuous formaldehyde solution having a high concentration, therefore a product high in content of trioxane, can be obtained, (3) no paraformaldehyde is deposited in the reactor or on the wall of the distilling column, (4) the reactor, the wall of the distilling column and the like are not corroded: therefore it is very advantageous for practical purposes.

DETAILED DESCRIPTION OF THE INVENTION

This invention is most characteristic in that a heteropolyacid is used as a reaction catalyst. This heteropolyacid is as shown in "Catalyst" vol. 18, No. 6, p. 169–177(1976), one having a mononuclear or polynuclear complex ion which has a diverse element (central element) in the center and is formed by the condensation of acid radicals with sharing an oxygen atom. The heteropolyacid is generally represented by the following chemical formula:

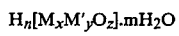

$$H_n[M_xM'_yO_z] \cdot mH_2O$$

wherein M is a central element, M' is a coordinating element and is generally one or more elements selected from the group consisting of W, Mo, V and Nb, x is a value of 0.1 to 10, y is a value of 6 to 30, z represents the number of oxygen atoms in the heteropolyacid and is a value in th range from about 10 to 80, n represents the number of acidic hydrogen atoms in the heteropolyacid and is a value larger than 1, and m represents the number of moles of water of crystallization and has a value in the range from 0 to about 40. The so-called mixed heteropolyacids containing two or more kinds of coordinating elements are also included in the heteropolyacids of this invention.

The central element M in the above-mentioned chemical formula generally consists of one or more elements selected from the group consisting of P, B, Si, Ge, Sn, As, Sb, U, Mn, Re, Cu, Ni, Co, Fe, Ce, Tn and Cr. Heteropolyacids which are particularly preferably used are those in which the central element M is P, Si, B, Ge, Cu or Sn, and among them those in which M is Si or P are particularly preferred.

The coordinating element M' in the above-mentioned chemical formula consists of one or more elements selected from the group consisting of W, Mo, V and Nb, though heteropolyacids which are particularly preferably used are those in which the coordinating element M' is W, Mo, V or a mixture thereof. Any of heteropolyacids within the above-mentioned range can accomplish the object of this invention, though particularly preferable ones among them are tungstosilicic acid, molybdosilicic acid, tungstophosphric acid, molybdophosphoric acid and mixtures thereof.

When these heteropolyacids are used, the trioxane content in the distillate obtained by distilling the reaction solution after the reaction is high, and its contents of by-products such as formic acid, methyl formate, methylal, methanol and the like are low. The distillation referred to here is distillation at the boiling point of the reaction solution.

In this invention, hydrous formaldehyde having a formaldehyde concentration of 95% by weight or lower may be used as a starting mterial. Needless to say, there may also be used, as starting meterial, compounds from which formaldehyde is formed by heating, such as paraformaldehyde, α-polyoxymethylene and the like. In particular, in order to practice this invention effectively, it is preferable to use hydrous formaldehyde having a formaldehyde concentration of 30 to 80% by weight.

In the reaction of this invention, formaldehyde is heated and reacted in the presence of a heteropolyacid, and the reaction conditions are as follows. The proportion of the heteropolyacid to the starting material in the reactor is usually 5 to 600 parts by weight, preferably 30 to 400 parts by weight, particularly preferably 100 parts by weight or more of a heteropolyacid to 100 parts by weight of a 30–80 wt % aqueous solution of formaldehyde. The reaction temperature at the time of reaction under heating is preferably 60° to 200° C., though an effective method is to effect the reaction by heating at the boiling point of the reaction solution, i.e., at about 100° C. However, the boiling point varies when pressure is applied or the pressure is reduced, and it varies depending also upon the proportion of formaldehyde, water and a heteropolyacid to one another in the reaction solution.

Next, the advantages of this invention are described below.

In the first place, the selectivity and the degree of conversion are high in the reaction according to this invention (the selectivity referred to here means the proportion of trioxane to all the products distilled out, and hence is expressed by the equation:

$$\text{Selectivity} = \frac{\text{Amount of trioxane}}{\text{Total amount of (trioxane + formic acid + methyl formate + methylal + methanol)}} \times 100\ (\%)$$

and the degree of conversion means the proportion of the reacated formaldhyde to the starting formaldehyde). For example, when, as shown in Example 1, 10 parts by weight of tungstosilicic acid is addd to a 60% by weight aqeuous formaldehyde solution and the resulting mixture is heated and reacted at atmospheric pressure, the sum of the amounts of by-products, methylal, methyl formate, formic acid and methanol may be limited to 1% or less and side reactions are greatly suppressed as compared with the case of using a sulfuric acid catalyst which is usually used. This means that no impurities accumulate in the reactants, and hence is very advantageous for purifying the trioxine. The trioxane content in the distillate taken out from the reactor is high, which means that the amount of the unreacted material is small, and hence is not only advantageous for purifying trioxane but also economical of energy. As mentioned above, the method of this invention is advantageous for industrial application.

In the second place, even when the concentration of starting formaldehyde to be used is high, no precipitate of paraformaldehyde adheres to the inside of the reactor. In the case of using a sulfuric acid catalyst which is usually used, when the formaldehyde concentration at the time of the reaction is increased, for example, to 60% by weight or higher, precipitates and scales of paraformaldehyde are formed in the reactor, and when the sulfuric acid concentration is increased in order to increase the formaldehyde concentration to 60% by weight or higher, the production of by-products is greatly increased and this becomes a problem in effecting the reaction on an industrial scale. On the other hand, according to the method of this invention, the formaldehyde concentration in the reaction solution can be increased, so that the trioxane content in the vapor distilled out can be increased. This is because the solubility of formaldehyde increases in proportion as the concentration of the heteropolyacid increases, and because when a high concentration of a heteropolyacid is allowed to coexist with formaldehyde, it becomes possible to synthesize trioxane from an aqueous formaldehyde solution having a higher concentration. Furthermore, for example, when a heteropolyacid is present in an amount of 100 parts by weight or more per 100 parts by weight of an aqeuous formaldehyde solution having a concentration of 30 to 80% by weight, it also becomes possible to synthesize trioxane from an aqueous formaldehyde solution having a concentration of 60% by weight or higher, for example, 80% by weight without the formation of precipitates of paraformaldehyde. It is presumed that the heteropolyacid thus acts as a catalyst for the synthesis of trioxane from formaldehyde, however it is difficult to say that the mechanism of its action has become clear. According to the method mentioned above, the water content in the product distilled out from the reactor is decreased so that trioxane having a very high concentration can be obtained, and no paraformaldehyde precipitates in the reactor, therefore an industrially advantageous process can be realized.

In the third place, the heteropolyacid used in this invention does not corrode the material for the apparatus which is industrially used. It is a fact universally known by those skilled in the art that well-known strong acid catalysts which are generally used are remarkably corrosive under the reaction conditions, therefore other measures are necessary for industrial application, and this is an important problem. However, heteropolyacids are noncorrosive at least at a concentration within the range mentioned in this invention, and cause no troubles in practical application.

In practicing this invention industrially, it is proper to use a rectifying column by connecting it onto the reactor containing a catalyst. When a starting aqeuous formaldehyde solution is continuously fed to the reactor at a constant flow rate, a vapor or solution containing trioxane can be taken out from the top of the rectifying column at a flow rate corresponding to the feeding rate. In the reactor, the aqueous formaldehyde solution is boiling in the presence of the catalyst, however the catalyst is hardly effused from the reactor, therefore when the amount of the reaction solution in the reactor is kept constant, the operation can be performed keeping the average reaction time constant. The proportion of the catalyst to the starting material mentioned above can be shown as a proportion in the reactor even in the case of such a flow reaction.

This invention is further explained below in more detail referring to examples.

EXAMPLE 1

To a reactor were charged 100 parts by weight of a 60% by weight aqueous solution (containing 0.5% by weight of methanol) of formaldehyde prepared from commercially available paraformaldehyde and 10 parts by weight of tungstosilicic acid, and they were heated and distilled. A rectifying column was attached to the reactor, after which a 60% by weight aqueous formaldehyde solution was continuously fed to the reactor so that the amount of the reaction solution in the reactor might always be constant, and the reaction solution was heated so that the temperature of the distilled might be 93° to 97° C. The distillate was sampled and examined for its composition. The results 3 hours after the initiation of the reaction are shown in Table 1. For comparison, an experiment was carried out in the same manner as above except that in place of the tungstosilicic acid, 10 parts by weight of sulfuric acid was allowed to coexist with the formaldehyde. As is obvious from Table 1, the use of tungstosilicic acid resulted in not only a higher trioxane content in the product, i.e., a higher degree of conversion in the reaction but also less side reactions, as compared with the use of sulfuric acid.

TABLE 1

| Catalyst Component | Tungstosilicic acid (10 parts by weight) | Sulfuric acid* (10 parts by weight) |
| --- | --- | --- |
| Trioxane | 42.0 | 31.4 |
| Water | 39.5 | 40.0 |
| Formaldehyde | 18.0 | 25.0 |
| Methyl formate | 0.01 | 1.2 |
| Methylal | 0.01 | 0.8 |
| Methanol | 0.5 | 1.2 |
| Formic acid | — | 0.4 |

Percentage of each component is by weight.
*is a comparative example.

EXAMPLE 2

Each of various heteropolyacids was allowed to coexist with 100 parts by weight of a 60% by weight aqueous formaldehyde solution, and the composition of the product was examined by using the same method as in Example 1. The reaction was effected while controlling the temperature of the vapor distilled out so as to be 93° TO 97° C. The results 3 hours after the initiation of the reaction are shown in Table 2. Further, the formation of scales in the reaction system was also examined. The selectivity referred to in Table 2 means, as described above, the proportion of trioxane to all the products distilled out and hence is expressed by the equation:

$$\text{Selectivity} = \frac{\text{Amount of trioxane}}{\text{Total amount of (trioxane + formic acid + methyl formate + methylal + methanol)}} \times 100\ (\%)$$

TABLE 2

| Catalyst acid | Catalyst acid (parts by weight) | Aqueous formaldehyde solution (parts by weight) | Trioxane content in the distillate (% by weight) | Selectivity (%) | Formation of scales |
| --- | --- | --- | --- | --- | --- |
| Tungstosilicic acid ($H_4SiW_{12}O_{40}\cdot XH_2O$) | 30 | 100 | 44 | 99.86 | none |
| Tungstosilicic acid ($H_4SiW_{12}O_{40}\cdot XH_2O$) | 100 | 100 | 46 | 99.78 | none |
| Tungstophosphoric acid ($H_3PW_{12}O_{40}\cdot XH_2O$) | 30 | 100 | 43 | 99.80 | none |
| Tungstophosphoric acid ($H_3PW_{12}O_{40}\cdot XH_2O$) | 100 | 100 | 45 | 99.81 | none |
| Molybdosilicic acid ($H_4SiMo_{12}O_{40}\cdot XH_2O$) | 30 | 100 | 42 | 99.85 | none |
| Molybdosilicic acid ($H_4SiMo_{12}O_{40}\cdot XH_2O$) | 100 | 100 | 46 | 99.82 | none |
| Molybdophosphoric acid ($H_3PMo_{12}O_{40}\cdot XH_2O$) | 30 | 100 | 41 | 99.88 | none |
| Molybdophosphoric acid ($H_3PMo_{12}O_{40}\cdot XH_2O$) | 100 | 100 | 45 | 99.80 | none |
| Vanadosilicic acid | 30 | 100 | 37 | 99.70 | none |
| Vanadophosphoric acid | 30 | 100 | 36 | 99.67 | none |
| Tungstogermanic acid | 30 | 100 | 36 | 99.55 | none |
| Tungstoboric acid | 30 | 100 | 34 | 99.52 | none |
| Molybdocupric acid | 30 | 100 | 35 | 99.51 | none |
| Molybdostannic acid | 30 | 100 | 36 | 99.57 | none |
| Vanadomolybdophosphoric acid ($H_4PVMo_{11}O_{40}\cdot XH_2O$) | 30 | 100 | 37 | 99.58 | none |
| Sulfuric acid (Comparative Example) | 30 | 100 | 34 | 95.30 | formed |
| Sulfuric acid (Comparative Example) | 50 | 100 | 36 | 93.15 | formed |

EXAMPLE 3

Various parts by weight of tungstosilicic acid or tungstophosphoric acid was added to 100 parts by weight of a 60% by weight aqueous formaldehyde solution, and the composition of the product was examined by the same method as in Example 2. The temperature of the distillate was controlled so as to be 93° to 97° C., and the reaction results 3 hours after the initiation of the reaction are shown in Table 3.

TABLE 3

| Heteropolyacid | Concentration (parts by weight) | Gaseous trioxane concentration (% by weight) | Selectivity (%) | Formation of scale |
|---|---|---|---|---|
| Tungstosilicic acid ($H_3SiW_{12}O_{40} \cdot XH_2O$) | 3 | 30 | 99.91 | none |
| | 5 | 37 | 99.85 | |
| | 10 | 42 | 99.88 | |
| | 30 | 44 | 99.86 | |
| | 100 | 46 | 99.78 | |
| | 200 | 47 | 99.75 | |
| | 300 | 48 | 99.70 | |
| | 400 | 48 | 99.75 | |
| | 500 | 47 | 99.70 | |
| | 600 | 45 | 99.65 | |
| Tungstophosphoric acid ($H_3PW_{12}O_{40} \cdot XH_2O$) | 3 | 29 | 99.90 | none |
| | 5 | 36 | 99.86 | |
| | 10 | 41 | 99.84 | |
| | 30 | 43 | 99.80 | |
| | 100 | 45 | 99.81 | |
| | 200 | 47 | 99.78 | |
| | 300 | 47 | 99.67 | |
| | 400 | 47 | 99.70 | |
| | 500 | 46 | 99.65 | |
| | 600 | 45 | 99.67 | |

EXAMPLE 4

Aqueous formaldehyde solutions were prepared so that the concentration of formaldehyde might be 25, 30, 40, 55, 60, 64, 70, 73, 75 and 80% by weight, respectively, and 400 parts by weight of tungstosilicic acid was added to 100 parts by weight of each of said aqueous solutions, after which the resulting mixture was heated and reacted in a reactor, and the composition of the product was examined by the same method as in Example 1. The reaction was effected while controlling the temperature of the vapor distilled out so as to be 93° to 97° C., and the reaction results 3 hours after the initiation of the reaction are shown in Table 4. In cases of all the formaldehyde concentrations tested, formaldehyde was uniformly dissolved.

TABLE 4

| Concentration of starting formaldehyde (% by weight) | Concentration of product trioxane (% by weight) | Selectivity (%) |
|---|---|---|
| 25 | 10 | 99.91 |
| 30 | 18 | 99.95 |
| 40 | 26 | 99.90 |
| 55 | 41 | 99.85 |
| 60 | 48 | 99.87 |
| 64 | 53 | 99.84 |
| 70 | 61 | 99.67 |
| 73 | 64 | 99.48 |
| 75 | 67 | 99.42 |
| 80 | 68 | 99.40 |

EXAMPLE 5

Each of various kinds of aqueous acid solutions was placed in a vessel made of SUS 304 and heated in an oil bath at 140° C., and the condition of the surface of the vessel which was in contact with the acid solution was observed with the lapse of time. In the case of an aqueous sulfuric acid solution, the SUS surface lost its luster with the lapse of time, and was corroded. The results are shown in Table 5.

TABLE 5

| Acid | | Corrosion of SUS surface | | |
|---|---|---|---|---|
| | | 1 hour | 5 hours | 3 days |
| Sulfuric acid | 5% | + | + | +++ |
| " | 30% | ++ | +++ | +++ |
| Tungstosilicic acid | 10% | − | − | − |
| " | 30% | − | − | − |
| " | 90% | − | − | − |
| Tungstophosphoric acid | 90% | − | − | − |
| Molybdosilicic acid | 90% | − | − | − |
| Molybdophosphoric acid | 90% | − | − | − |
| Tungstogermanic acid | 90% | − | − | − |
| Vanadosilicic acid | 90% | − | − | − |

+ express barely detectable corrosion
++ express clearly detectable corrosion
+++ express serious corrosion
− express a negative result, i.e., no corrosion

EXAMPLE 6

Each of various kinds of aqueous acid solutions was placed in a vessel made of SUS 304 and heated in an oil bath at 140° C., and the change of color of the aqueous acid solution was observed with the lapse of time. In the case of an aqueous sulfuric acid solution, the solution was colored (blue) by the release of metal ions which was caused by the corrosion of SUS. The results are shown in Table 6, wherein + expresses coloration, the number of + expresses the degree of coloration, and − expresses a negative result, i.e., no coloration.

TABLE 6

| Acid | | Coloration of an aqueous acid solution | | |
|---|---|---|---|---|
| | | 1 hour | 5 hours | 3 days |
| Sulfuric acid | 5% | + | + | +++ |
| " | 30% | +++ | +++ | +++ |
| Tungstosilicic acid | 90% | − | − | − |
| Tungstophosphoric acid | 90% | − | − | − |

What is claimed is:

1. A method of synthesizing trioxane which comprises heating formaldehyde at a temperature from 60° to 200° C. in the presence of an aqueous solution of a heteropolyacid of the formula $$H_n(M_xM'_yO_z) \cdot mH_2O$$

wherein
M is at least one member selected from the group consisting of P and Si,
M' is at least one member selected from the group consisting of Mo, V and Nb,
x is from 0.1 to 10,
y is from 6 to 30,
z is from 10 to 80,
n is more than 1, and
m is from 0 to 40.

2. A method for synthesizing trioxane according to claim 1, wherein the heteropolyacid is selected from the group consisting of molybdosilicic acid, molybdophosphoric acid and mixtures of these acids.

3. A method for synthesizing trioxane according to claim 1, wherein the formaldehyde is hydrous formaldehyde having a concentration of 30 to 80% by weight.

4. A method for synthesizing trioxane according to claim 3, wherein the heteropolyacid is used in an amount of 5 to 600 parts by weight per 100 parts by weight of the aqueous formaldehyde solution.

5. A method for synthesizing trioxane according to claim 3, wherein the heteropolyacid is used in an amount of 100 to 600 parts by weight per 100 parts by weight of the aqueous formaldehyde solution.

6. A method of synethesizing trioxane which comprises heating formaldehyde at a temperature from 60° to 200° C. in the presence of an aqueous solution of a heteropolyacid of the formula $$H_n(M_xW_yO_z)\cdot mH_2O$$

wherein
M is at least one member selected from the group consisting of B and Ge,
x is from 0.1 to 10,
y is from 6 to 30,
z is from 10 to 80,
n is more than 1, and
m is from 0 to 40.

7. A method for snythesizing trioxane according to claim 6, wherein the formaldehyde is hydrous formaldehyde having a concentration of 30 to 80% by weight.

8. A method for synthesizing trioxane according to claim 7, wherein the heteropolyacid is used in an amount of 5 to 600 parts by weight per 100 parts by weight of the aqueous formaldehyde solution.

9. A method for synthesizing trioxane according to claim 7, wherein the heteropolyacid is used in an amount of 100 to 600 parts by weight per 100 parts by weight of the aqueous formaldehyde solution.

10. A method of synthesizing trioxane which comprises heating formaldehyde at a temperature from 60° to 200° C. in the presence of an aqueous solution of a heteropolyacid of the formula $$H_n(M_xMo_yO_z)\cdot mH_2O$$

wherein
M is at least one member selected from the group consisting of Sn and Cu,
x is from 0.1 to 10,
y is from 6 to 30,
z is from 10 to 80,
n is more than 1, and
m is from 0 to 40.

11. A method for synthesizing trioxane according to claim 10, wherein the formaldehyde is hydrous formaldehyde having a concentration of 30 to 80% by weight.

12. A method for synthesizing trioxane according to claim 11, wherein the heteropolyacid is used in an amount of 5 to 600 parts by weight per 100 parts by weight of the aqueous formaldehyde solution.

13. A method for synthesizing trioxane according to claim 11, wherein the heteropolyacid is used in an amount of 100 to 600 parts by weight per 100 parts by weight of the aqueous formaldehyde solution.

* * * * *